(12) United States Patent
Abdellatif et al.

(10) Patent No.: US 10,551,296 B2
(45) Date of Patent: *Feb. 4, 2020

(54) INTEGRATED ULTRASONIC TESTING AND CATHODIC PROTECTION MEASUREMENT PROBE

(71) Applicant: Saudi Arabian Oil Company, Dhahran (SA)

(72) Inventors: Fadl Abdellatif, Thuwal (SA); Hamad Al-Saiari, Thuwal (SA); Ali Outa, Thuwal (SA); Ayman Amer, Thuwal (SA); Sahejad Patel, Thuwal (SA); Ameen Obedan, Thuwal (SA); Hassane Trigui, Thuwal (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 16/119,089

(22) Filed: Aug. 31, 2018

(65) Prior Publication Data
US 2018/0372615 A1 Dec. 27, 2018

Related U.S. Application Data

(63) Continuation of application No. 15/342,791, filed on Nov. 3, 2016, now Pat. No. 10,234,375.

(Continued)

(51) Int. Cl.
*G01B 17/02* (2006.01)
*G01N 29/22* (2006.01)
(Continued)

(52) U.S. Cl.
CPC ............. *G01N 17/02* (2013.01); *B63G 8/001* (2013.01); *C23F 13/04* (2013.01); *C23F 13/22* (2013.01);
(Continued)

(58) Field of Classification Search
CPC ...... C23F 13/04; C23F 13/22; C23F 2213/31; G01R 19/0092; G01N 29/245;
(Continued)

(56) References Cited

U.S. PATENT DOCUMENTS

| 6,317,387 | B1 | 11/2001 | D'Amaddio et al. |
| 9,233,466 | B2 | 1/2016 | Skrinde |
| 10,234,375 | B2 * | 3/2019 | Abdellatif ............... C23F 13/04 |

FOREIGN PATENT DOCUMENTS

| EP | 2762401 A1 | 8/2014 |
| WO | WO 2010/146360 | 12/2010 |
| WO | WO 2016/020677 | 2/2016 |

* cited by examiner

*Primary Examiner* — Jacques M Saint Surin
(74) *Attorney, Agent, or Firm* — Leason Ellis LLP

(57) ABSTRACT

This application discloses integrated probes and probe systems, which can be attached to the robotic arms of a remotely operated vehicle to perform both cathodic protection (CP) voltage measurements and ultrasonic testing (UT) thickness measurements at an underwater surface. In some embodiments, the integrated probe system couples an inner and outer gimbal together such that one or more electrically conductive legs pass from the outer gimbal through the inner gimbal. These legs are arranged about an ultrasonic sensor which extends from the front surface of the inner gimbal. When the integrated probe contacts the underwater surface, both the ultrasonic sensor and at least one leg contact the surface, thereby providing substantially simultaneous CP and UT measurements.

20 Claims, 5 Drawing Sheets

Related U.S. Application Data

(60) Provisional application No. 62/395,162, filed on Sep. 15, 2016.

(51) Int. Cl.
*C23F 13/04* (2006.01)
*G01N 29/24* (2006.01)
*G01N 29/265* (2006.01)
*G01R 19/00* (2006.01)
*B63G 8/00* (2006.01)
*C23F 13/22* (2006.01)
*G01N 17/02* (2006.01)

(52) U.S. Cl.
CPC ........... *G01B 17/02* (2013.01); *G01B 17/025* (2013.01); *G01N 29/225* (2013.01); *G01N 29/226* (2013.01); *G01N 29/245* (2013.01); *G01N 29/265* (2013.01); *G01R 19/0092* (2013.01); *B63G 2008/005* (2013.01); *C23F 2213/31* (2013.01); *G01N 2291/0231* (2013.01); *G01N 2291/02854* (2013.01); *G01N 2291/101* (2013.01)

(58) Field of Classification Search
CPC .... G01N 29/226; G01N 17/02; G01N 29/265; G01N 29/225; G01N 29/043; G01N 2291/0234; G01N 2291/02854; G01N 2291/0231; G01N 2291/101; G01B 17/025; G01B 17/02; B63G 8/001; B63G 2008/005
USPC .......................................................... 73/628
See application file for complete search history.

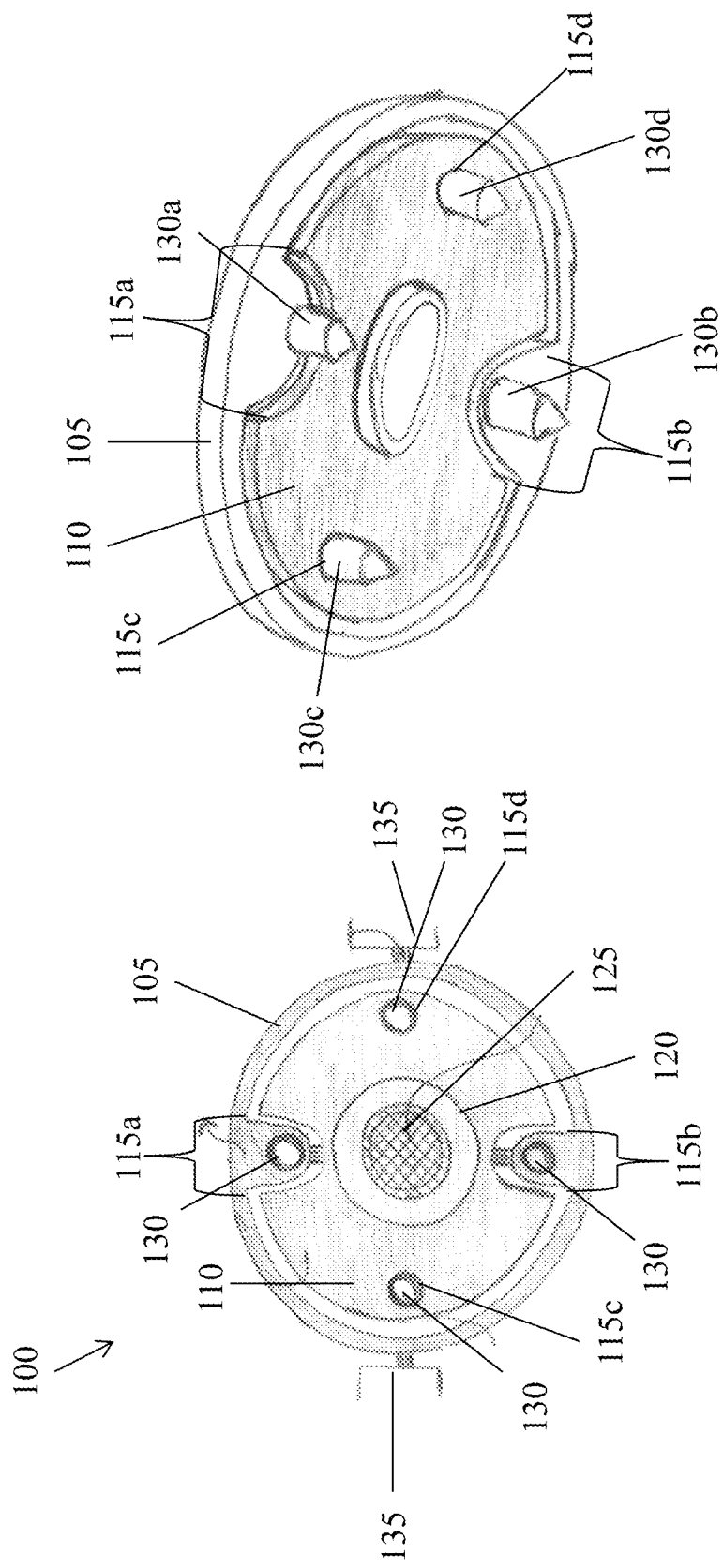

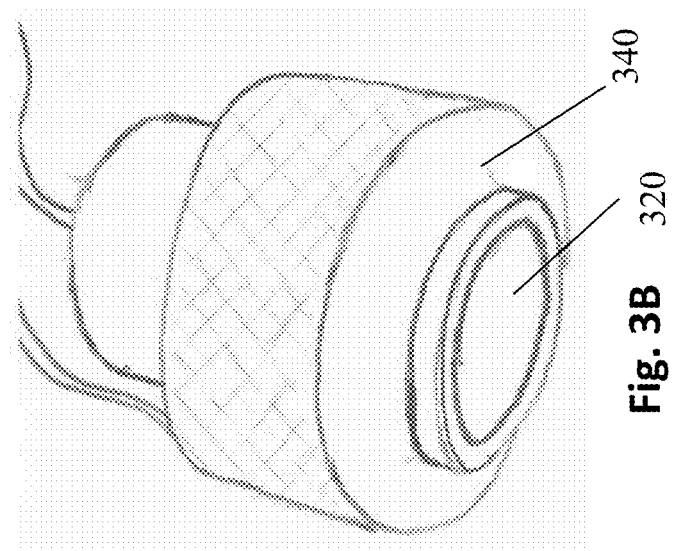
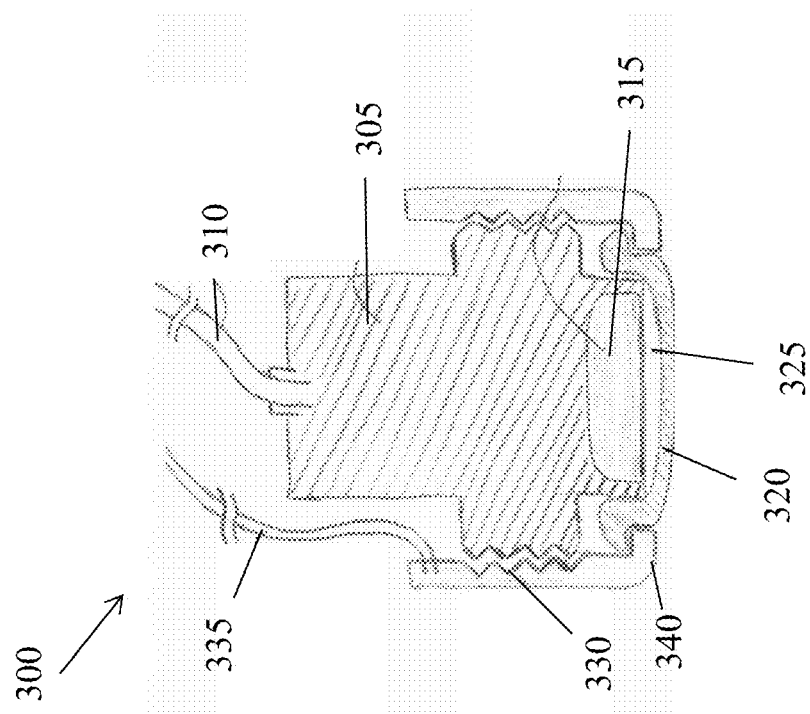

INTEGRATED ULTRASONIC TESTING AND CATHODIC PROTECTION MEASUREMENT PROBE

CROSS-REFERENCE TO RELATED APPLICATIONS

This application is a continuation of U.S. application Ser. No. 15/342,791, filed Nov. 3, 2016, which is based on and claims priority under 35 U.S.C. § 119 to U.S. Provisional Application Ser. No. 62/395,162, filed Sep. 15, 2016, each of which is hereby incorporated by reference as if expressly set forth in their respective entireties herein.

FIELD OF THE INVENTION

This patent application generally relates to testing and measuring mechanisms, and more particularly to probe systems for ultrasonically measuring thickness and performing cathodic protection voltage readings in an underwater environment.

BACKGROUND

In order to non-destructively measure the thickness of a structure, one common practice is to have a measuring device emit ultrasonic waves at the surface of the structure and to measure the time it takes for the ultrasonic wave to return to the measuring device. Ultrasonic testing ("UT") is applicable for measuring the thickness of metal structures, such as underwater structures like boat hulls, pilings, pipelines, and risers. In order to limit corrosive effects to such underwater surfaces, the technique of cathodic protection ("CP") is applied. In CP, the metal surface of the underwater structure is made into a cathode of an electrochemical cell (e.g., a Galvanic cell) and the surface is coated with another metal having a greater negative electrode potential (e.g., zinc, magnesium, aluminum) that functions as an anode. Then, the anodic metal corrodes, but the structure surface does not. To ensure that CP is working as intended, it is common to measure the voltage at the surface of the structure. Typically, for underwater structures, a remotely operated vehicle ("ROV") or human diver is used to perform CP and UT measurements. In either case, due to load and logistical limitations inherent with conventional ROVs, CP and UT measurements are performed by two probes at separate ROV robotic arms or by exchanging one probe for another at a single arm. In either case, the switching or readjusting of probes to perform repeated CP and/or UT measurements is time consuming and costly. Additionally, due to the weight of conventional CP and UT probe systems and the need for a two-armed ROV system, only larger Work-Class ROVs are capable of attaching two arms to alternatingly perform both measurements in a single trip. However, Work-Class ROVs are unsuitable for shallow and limited accessibility (e.g., surfaces within small cavities) inspection sites. Thus, there is a need for an integrated CP and UT probe system that can be coupled to smaller and lighter ROVs having only a single robotic arm.

It is in regard to these issues that the present application is provided.

SUMMARY OF THE INVENTION

According to a broad aspect of the invention, integrated probe systems are provided that can substantially simultaneously perform both cathodic protection (CP) voltage readings and ultrasonic testing (UT) thickness measurements.

In accordance with one aspect of the invention, embodiments of the integrated probe systems include an outer gimbal having a front surface and a rear surface, and an inner gimbal coupled to the outer gimbal to provide at least one degree of freedom. The inner gimbal can include a front surface defining a cavity therein, and the inner gimbal can be shaped to define one or more ingresses that pass crosswise between the front and rear surfaces of the inner gimbal. In some embodiments, the ingresses are defined by the inner gimbal to be indentations formed along a circumference of the inner gimbal. In other embodiments, the ingresses are defined by the inner gimbal to be apertures transversely formed through the inner gimbal. In one or more embodiments, the integrated probe system includes an articulated carrier having a first end integrally formed with the rear surface of the inner gimbal and a ball caster disposed at a second end, in which the ball caster couples to the outer gimbal to provide the at least one degree of freedom to the inner gimbal.

Continuing with this aspect of the invention, in one or more embodiments, the integrated probe system includes a sensor housing seated in the cavity of the inner gimbal. An ultrasonic probe is within the sensor housing, the ultrasonic probe having a transducer crystal and a flexible membrane arranged about the transducer crystal, and a couplant disposed within a gap between the flexible membrane and the transducer crystal. Further, one or more legs, which each have an electrically conductive tip and a subsea housing containing a reference electrode, extend longitudinally away from the outer gimbal via the one or more ingresses and are arranged about the ultrasonic probe, such that the one or more legs are passively adjustable in response to a force imparted when the one or more legs contact the underwater surface.

In accordance with another aspect of the invention, embodiments of the integrated probe system include an ultrasonic sensor body, an ultrasonic testing cable disposed at a first end of the ultrasonic sensor body, and an ultrasonic probe disposed at a second end of the ultrasonic sensor body. In one or more embodiments, the ultrasonic probe includes an ultrasonic element and a flexible membrane adjacently spaced about the ultrasonic sensor body to define a gap between the ultrasonic element and the flexible membrane, in which the gap is filled with a couplant. Further, the integrated probe system can include a housing that defines an aperture therethrough, in which the aperture is centrally located in the housing and in which the ultrasonic probe is seated in the aperture, and the housing further including an electrically conductive portion. Additionally, the integrated probe system includes conductive leads connected to and extending from the electrically conductive portion.

In accordance with a further aspect of the invention, embodiments of a system for performing cathodic protection voltage readings and ultrasonic testing thickness measurements at an underwater surface substantially simultaneously are provided. The system includes a remotely operated underwater vehicle having a measuring arm, with an end effector disposed at a free end of the measuring arm. Additionally, the system includes an integrated probe for measuring cathodic protection voltage and ultrasonic testing thickness measurement coupled to the end effector. In one or more embodiments, the integrated probe includes an outer gimbal having a front surface and a rear surface, and an inner gimbal coupled to the outer gimbal to provide at least one degree of freedom. The inner gimbal has a front surface that defines a cavity therein, and the inner gimbal is shaped to define one or more ingresses that pass crosswise between the front and rear surfaces of the inner gimbal. The integrated probe further includes a sensor housing seated in the cavity of the inner gimbal, and an ultrasonic probe disposed within the sensor housing, in which the ultrasonic probe includes a flexible membrane arranged about a transducer crystal such that a gap is defined therebetween and filled with a couplant. Further, a voltage electrode is communicatively coupled to a reference electrode, in which the voltage electrode is disposed at the end effector or the integrated probe, and the reference electrode is disposed within the remotely operated underwater vehicle.

In accordance with an additional aspect of the invention, embodiments of a method of performing cathodic protection voltage readings and ultrasonic testing thickness measurements on an underwater surface with an integrated probe having an ultrasonic probe and at least one leg with an electrically conductive tip are provided. The method includes positioning a remotely operated vehicle, which has at least one robotic arm with an arm end effector disposed at a free end of the robotic arm and the integrated probe coupled to the arm end effector, in proximity to the underwater surface. The method then includes contacting the underwater surface with the integrated probe and orienting the integrated probe transverse to the underwater surface such that the ultrasonic probe and the at least one leg with an electrically conductive tip contacts the underwater surface. Then, the method continues by measuring, by the at least one leg, a voltage at the underwater surface, and measuring, by the ultrasonic probe, a thickness of the underwater surface. Further, in one or more embodiments, the method then includes processing, by a signal conditioner housed within the remotely operated vehicle, the voltage and the thickness of the underwater surface to produce a data file. The method continues by transmitting the data file to a data acquisition unit housed within the remotely operated vehicle. Additionally, the method includes processing, by the data acquisition unit, the data file to record, review, or analyze the voltage and thickness of the underwater surface.

In accordance with a still further aspect of the invention, embodiments of the integrated probe systems include a probe carrier that has at least one degree of freedom relative to a static base, and a rear surface coupled to the static base and a front surface having an electrically conductive portion and defining a cavity therein. Further, the electrically conductive portion can include one or more legs arranged about the ultrasonic probe, each leg having an electrically conductive tip and a subsea housing containing a reference electrode, and which extend longitudinally away from the probe carrier, in which the one or more legs are passively adjustable in response to a force imparted when the one or more legs contact the underwater surface. In one or more embodiments, the integrated probe systems include a sensor housing seated in the cavity of the probe carrier and an ultrasonic probe disposed within the sensor housing, the ultrasonic probe having a transducer crystal and a flexible membrane arranged about the transducer crystal, and a couplant disposed within a gap between the flexible membrane and the transducer crystal.

BRIEF DESCRIPTION OF THE DRAWINGS

The accompanying drawing figures illustrate exemplary embodiments and are not intended to be limiting of the invention. Among the drawing figures, like references are intended to refer to like or corresponding parts.

FIG. 1A illustrates a front view of an integrated CP and UT probe system in accordance with at least one embodiment of the present application;

FIG. 1B illustrates an isometric side view of the integrated CP and UT probe system of FIG. 1A;

FIG. 3A illustrates a top cutaway view of an integrated CP and UT probe in accordance with another alternate embodiment of the present application;

FIG. 3B illustrates an isometric side view of the integrated CP and UT probe of FIG. 3A;

DETAILED DESCRIPTION OF CERTAIN EMBODIMENTS OF THE INVENTION

Figure 2B:
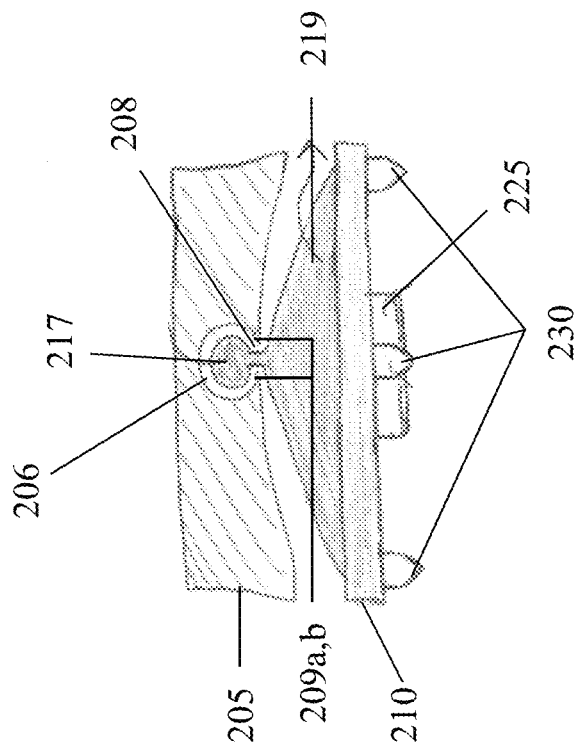
FIG. 2B illustrates a side view of the alternate probe system of FIG. 2A.

The invention is now described with reference to the accompanying drawings, which form a part hereof, and which show, by way of illustration, example implementations and/or embodiments of the present invention. It is to be understood that other embodiments can be implemented and structural changes can be made without departing from the spirit of the present invention. Among other things, for example, the disclosed subject matter can be embodied as methods, devices, components, or systems.

Furthermore, it is recognized that terms may have nuanced meanings that are suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter can be based upon combinations of individual example embodiments, or combinations of parts of individual example embodiments.

In accordance with the present application, embodiments are provided that are directed to integrated probes and integrated probe systems for measuring cathodic protection (CP) voltage and measuring surface thickness using ultrasonic testing (UT) in which the delay between taking each measurement is minimized. In this way, CP and UT measurements can be performed substantially simultaneously. For example, both CP and UT measurements can be performed during a single touchdown at a specific underwater surface (or an "inspection surface"), such as an underwater pipeline or piling, or the underside of a moored ship hull.

In one aspect, the integrated probes as provided in one or more embodiments herein can be coupled to a single robotic arm of a remotely operated vehicle (ROV) at, for example, the free end of an arm-end effector. The structural limitations of typical ROVs restrict their robotic arms to only a single interchangeable or permanently mounted probe per robotic arm, and such arms lack the dexterity necessary to perform simultaneous CP and UT measurements. Thus, conventionally, in order for a ROV to perform both CP and UT measurements in a single trip, it must have at least two robotic arms. Each robotic arm is heavy, and only large, work-class ROVs can include two or more robotic arms. In some cases, conventional measurement methods require a complete probe exchange (e.g., from CP to UT, or vice versa) at the arm to perform the second measurement. Such limited actuation capabilities result in inherent delay (and thus increased costs due to necessarily increased ROV time) because the two probe measurement systems must switch between two wholly separate CP and UT probes, and must reorient the second probe to the same inspection surface where the first probe measurement was taken. The present application does not require the implementation of two separate CP and UT probes or probe systems by separate robotic arms of a ROV or by requiring the exchange of probe attachments.

Further, the integrated probe systems herein provide the advantage of being implementable by small, lightweight class ROVs having only a single robotic arm, such as electric ROVs, general class ROVs, inspection class ROVs, and observation class ROVs. Smaller class ROVs can be necessary if the inspection surface has accessibility issues (e.g., shallow water sites), or if there are power supply limitations.

In one or more embodiments, the integrated probe system includes a central UT sensor or transducer (e.g., a piezo-ceramic crystal) with a surrounding array of electrically conductive legs having tips or fixtures that are articulated and passively adjustable. The electrically conductive legs are not rigid, but rather have some flexibility with respect to how they contact an underwater surface. In this way, when the electrically conductive legs contact an underwater surface, they passively adjust to orient the UT sensor transverse to the inspection surface. At the same time, the legs conduct the cathodic protection electrical voltage associated with the surface, such as with electrically conductive steel tips, thereby acting as a CP probe. In this way, CP and UT measurements can be conducted substantially simultaneously, thereby reducing measurement inspection time, the size and weight added to the robotic arm, and improving ROV agility.

Referring now to FIGS. 1A-B, an integrated probe system 100 for conducting cathodic protection voltage readings and ultrasonic testing thickness measurements at an underwater surface in accordance with one or more implementations of the present application is provided. Integrated probe 100 includes an outer gimbal 105 that functions as a base mount for coupling to a robotic arm. For example, the rear surface of the outer gimbal 105 can be coupled to a ROV measurement arm at an end effector or other static base, as is known in the art. The outer gimbal 105 is generally cylinder shaped, though rectangular, ellipsoid or other shapes can be implemented as appropriate. The outer gimbal 105 can be made of stainless steel or other alloy that is suitable for underwater inspection.

In one or more embodiments, an inner gimbal 110 is coupled to the outer gimbal 105. For example, the inner gimbal 110 is coupled to the outer gimbal 105 by one or more of: screws, threads, bolts, adhesives, male and female coupling members, joints, diaphragm coupling, ball and socket, cam and groove coupling or the like. The inner gimbal 110 can be made of stainless steel or other alloy that is suitable for underwater inspection. Preferably, the inner gimbal 110 is molded to define one or more ingresses 115a, 115b, 115c, 115d (and more generally ingresses 115), for one or more electrically conductive legs 130 to pass through or around the circumference of the inner gimbal. The electrically conductive legs 130 act as cathodic protection voltage electrodes. In one or more embodiments, the ingresses 115a, 115b are defined as indentations formed along a circumference of the inner gimbal 110, in a concave, rectangular, triangular, or other shape designed to facilitate the passive adjustment of legs 130. In one or more embodiments, the ingresses 115c, 115d are defined as apertures formed through the narrow, crosswise width of inner gimbal 110. For example, the aperture-type ingresses 115c, 115d can be a cross-section of the inner gimbal 110. Integrated probe 100 can also include a combination of indentation-type ingresses 115a, 115b and aperture-type ingresses 115c, 115d. In this way, different arrangements of the ingresses 115 and legs 130 defined by inner gimbal 110 can be contemplated that are more suitable for passively adjusting to a particular inspection surface. Moreover, the passage of the legs 130 through the ingresses 115 can serve to couple the inner gimbal 110 to the outer gimbal 105 in some embodiments.

A sensor housing 120 is implanted at the front surface of the inner gimbal 110 and depends at least partially beyond the front surface. In one or more embodiments, the sensor housing 120 is implanted at the front surface of the inner gimbal 110 in a cavity defined therein. For example, the sensor housing 120 can include a knurled ring made of stainless steel or other alloys, a flexible membrane and a locking ring connected in sequence. In one or more embodiments, the sensor housing 120 is located at the center of the inner gimbal 110. In one or more embodiments, the sensor housing 120 is located on a circumferential edge of the outer gimbal 105 or inner gimbal 110. An ultrasonic probe 125 is contained within the sensor housing 120 and arranged below the flexible membrane. In one or more embodiments, the ultrasonic probe 125 comprises a single piezo-ceramic crystal. In another embodiment, the ultrasonic probe 125 comprises a plurality of piezo-ceramic crystals. The ultrasonic probe 125 can be selected to emit and receive ultrasonic waves at a variety of particular frequencies. For example, the ultrasonic sensor can operate at frequencies of 2.0 MHz, 2.25 MHz, 3.5 MHz, 5.0 MHz, or 7.5 MHz. To facilitate ultrasonic transmission, a film of membrane couplant is located, for example, within a gap between the ultrasonic probe 125 and the flexible membrane of the sensor housing 120. Membrane couplant can comprise a viscous liquid, gel, or paste used to minimize the amount of air in the gap between the sensor and the membrane. For example, the membrane couplant can be propylene glycol, glycerin, silicone oil, or various commercially available gels.

The CP probe functionality of the integrated probe system 100 is provided by measuring the voltage difference between one or more reference electrodes (or "reference cells") and one or more voltage electrodes that contact the inspection surface. The reference electrode is kept electrically insulated from the voltage electrode and is typically submerged in water (such as the underwater environment itself). In one or more embodiments, CP probe functionality of the integrated probe system 100 is provided by one or more electrically conductive legs 130 that extend longitudinally beyond the front surface of the outer gimbal 105. The legs 130 can be integrally formed with the outer gimbal 105 or can be separate cathodic probes that are installed at the outer gimbal. In either case, the legs are articulated—i.e., connected to allow flexibility of movement. In one or more embodiments, the one or more legs 130 pass through one or more ingresses 115 defined by the inner gimbal 110. In one or more embodiments, the legs 130 include a subsea housing 131 that contains one or more reference cells within that serves as a reference electrode, and a conductive tip 132 at the end of the housing that serves as a voltage electrode. The conductive tip 132 is made of conductive metals, such as steel or other alloys that can conduct voltage at the underwater surface to be measured. The reference cell housed in the subsea housing 131 must be exposed to water and can be of the type used in conventional cathodic protection potential probe construction, such as a silver/silver chloride half cell or a pure zinc electrode. In other embodiments, the reference electrode is located at the outer surface of, or housed within, a ROV or its robotic arm. The electrically conductive legs 130 are in electrical connection with a voltage processing device, such as a voltmeter (not shown), which can be located at the integrated probe system 100, an ROV or surface-side in order to record and/or display voltage readings taken at a measurement site. In embodiments implementing an ROV, the ROV can have an umbilical cable leading to an above-surface location to couple, by an electrical cable, a voltmeter to the non-tip end of the legs 130, such that when the conductive tip 132 contacts the underwater surface (e.g., a pipeline), the potential is measured by the voltmeter. At least one voltage electrode at one of the tips 132 of legs 130 must be in contact with the inspection surface to obtain an accurate cathodic potential reading, but it is not necessary that each leg 130 be in contact with the inspection surface when the reading is made. The present application does not suffer from inaccurate readings due to various resistive paths presented by each leg 130 during voltage reading.

In one or more embodiments, the tips 132 of legs 130 are shaped as cones having circular or elliptical bases. In other embodiments, the tips 132 of legs 130 are pyramid shaped, rectangular prisms, semicircular, pointed, flat, or have rounded ends. In this way, the tips 132 are re-configurable or interchangeable to achieve various contact configurations. For example, the tips 132 can be mobile metallic rollers, wheeled tips or ball casters instead of static stainless steel tips. Such a configuration will reduce impact on a ROV arm end effector upon touchdown at an inspection surface (e.g., a steel surface of a pipe) and allow for translational motion across the inspection surface when performing scans instead of spot checks.

During operation of integrated probe system 100, in order to perform both CP and UT measurements substantially simultaneously, both the CP and UT aspects of the integrated probe system need to be brought into proximity to the inspection surface. Sufficient proximity is dependent upon the calibration of the ultrasonic probe 125, meaning that the ultrasonic probe has a certain effective measurement range as a result of the properties of water in between the probe and the surface, the materials of the surface, and other considerations. For example, the effective measurement range of the ultrasonic probe 125 means that it needs to abut or be within a few millimeters of the inspection surface to perform a successful measurement. If the ultrasonic probe 125 is any further from the inspection surface, it will lose signal integrity and fail to acquire a reading. In one or more embodiments, the ultrasonic probe 125 has an effective measurement range of 0-2 mm. The further that the ultrasonic probe 125 is from the inspection surface, the less accurate that the UT measurement is. In one or more embodiments, the electrically conductive legs 130 must contact the inspection surface in order to take a CP voltage measurement. As such, integrated probe system 100 can be arranged such that the legs 130 contact the inspection surface while ultrasonic probe 125 is positioned within its measurement effectiveness range (e.g., 0-2 mm from the inspection surface). The arrangement of legs 130 with regard to the ultrasonic probe 125 within the sensor housing 120 can be configured to accommodate the diameter or curvature of particular inspection surfaces. For example, in one or more embodiments, the legs 130 extend a distance beyond the sensor housing 120. In this way, when the integrated probe system 100 is brought in proximity to the inspection surface, one or more of the legs 130 will contact the surface, but the ultrasonic probe 125 will not, though the ultrasonic probe will still be close enough to the surface to be within its effective measurement range for performing accurate UT measurements. In one or more embodiments, the legs 130 extend 0.5 mm, 1 mm, 1.5 mm, 2 mm, or 2.5 mm beyond the sensor housing 120. In other embodiments, the legs 130 are aligned with the sensor housing 120. Longer legs 130 can be implemented for inspection surfaces having smaller diameters (e.g., approximately 10 cm or less) because for smaller inspection surfaces, the front surface width of the integrated probe system 100 is comparable to the inspection surface and thus not all the legs can contact the surface at once, though if at least one leg contacts the surface and the other legs are oriented to surround the surface, then the ultrasonic probe 125 will be oriented at the inspection surface within its effective measurement range.

The decision of whether and how much the legs 130 extend beyond the sensor housing 120 and where to arrange the legs at the front surface of the integrated probe system 100 can be dependent upon the particular arrangement desired. For example, the legs 130 can be advantageously arranged around a sensor housing 120 located in the center of the front surface of inner gimbal 110, such that each leg 130 is equidistant from both one another and the sensor housing. Centrally locating the sensor housing 120 in this way maximizes the likelihood that a UT thickness measurement is performed as one or more of the legs 130 contacts an inspection surface. The distance that the legs 130 are from the sensor housing 120 can be varied, depending on the arrangement desired to inspect a particular surface. For example, an arrangement in which the legs 130 are near to the sensor housing 120 decreases any differences in measurement lag between taking a CP voltage and UT thickness measurement and increases the precision of the spot inspection, whereas spacing the legs 130 relatively further from the sensor housing provides a wider inspection area and can provide an alignment assist (i.e., one leg contacts the surface and the inner gimbal 110 shifts in response to that force, thereby pushing one or more other legs into contact as well).

While the exemplary embodiments described herein include CP probes that are arranged to contact the inspection surface to perform voltage measurements, the invention is not limited to express contact CP probe types, such as legs 130, but can include non-contacting proximity CP probes. For example, a proximity CP probe can be implemented at the inner gimbal 110 in place of the legs 130. A proximity electrode is housed at the inspection tip of the proximity CP probe and a reference electrode is provided in the form of a "ground" wire that connects to the voltmeter (e.g., within an ROV or diver umbilical cord). A proximity CP probe typically has an effective measurement range on par with the ultrasonic probe 125 (e.g., 0-1 mm, 0-1.5 mm, 0-2 mm).

In one aspect of the present application, the integrated probe system 100 provides an advantage of being passively adjustable to the underwater surface to be measured. As such, one or more rotational joints 135 can be included in integrated probe system 100 to provide freedom of movement for the outer gimbal 105, the inner gimbal 110 and/or the electrically conductive legs 130. The rotational joints 135 can be hinged to the outer gimbal 105, the inner gimbal 110 or between the two. When the rotational joint 135 is hinged at a first end to the outer gimbal 105, the second end (i.e., the free end) of the rotational joint is coupled to a ROV measurement arm, static base or other external carrier (such as an arm end-effector). In one or more embodiments, the rotational joints 135 include two rotational joints that couple the outer gimbal 105 to an external carrier and two rotational joints that couple the inner gimbal 110 to the outer gimbal 105. The rotational joints 135 serve to effectively provide a combined two degrees of freedom to the ultrasonic probe 125, namely for the outer gimbal 105 to pitch around the side-to-side axis defined by a plane in the longitudinal diameter of the outer gimbal (the "pitch plane") and for the inner gimbal to 110 yaw around the vertical axis defined by a plane perpendicular to the longitudinal diameter of the outer gimbal (the "yaw plane").

In practice, when the electrically conductive legs 130 contact the inspection surface, the force imparted from the surface acts on the integrated probe system 100 to push a contacting leg or legs back and bring other legs into contact with the surface. In this way, additional legs 130 can be brought into contact with the inspection surface, thereby providing more accurate voltage measurements. The certain angular motion in the pitch and yaw planes provided by the arrangement of the rotational joints 135 of the integrated probe system 100 serves to improve leg 130 surface contact. For example, in one or more embodiments, the integrated probe system 100 can adjust by 0-15, 0-20, 0-30, or 0-45 degrees through the pitch or yaw planes.

In a particular embodiment illustrated by FIGS. 1A-1B, four articulated electrically conductive legs 130 are arranged around an ultrasonic probe 125. FIG. 1B illustrates a first pair of legs 130a, 130b that are diametrically opposed to one another and pass through indentation-type ingresses 115a, 115b defined by inner gimbal 110. A second pair of legs 130c, 130d is also diametrically opposed to one another and passes through aperture-type ingresses 115c, 115d defined by the circumferential edge of inner gimbal 110. In this embodiment, the four legs 130a-130d are equally spaced 90 degrees apart about the ultrasonic probe 125. This arrangement provides maximum range for at least one leg to be able to contact the inspection surface in order to obtain a voltage reading. However, depending on the particular application, other electrically conductive leg arrangements of four legs can be contemplated in which the legs are not equally spaced apart.

Furthermore, the flexibility of legs 130 in conjunction with the flexibility of inner gimbal 110 causes the ultrasonic probe 125 to be aligned on the inspection surface within a certain margin (e.g., the front surface of inner gimbal 110 is substantially transversely perpendicular to the target surface). This passive alignment of the ultrasonic probe 125 by the electrically conductive legs 130 allows both CP voltage and UT measurements to be performed simultaneously, or at least in a single probing of the inspection surface. In one or more embodiments, a proximity sensor is coupled with the ultrasonic probe 125 to aid in positioning at the inspection surface. For example, the proximity sensor can be an infrared or acoustic sensor located inside sensor housing 120 at or adjacent to the flexible membrane of ultrasonic probe 125.

Figure 2A:
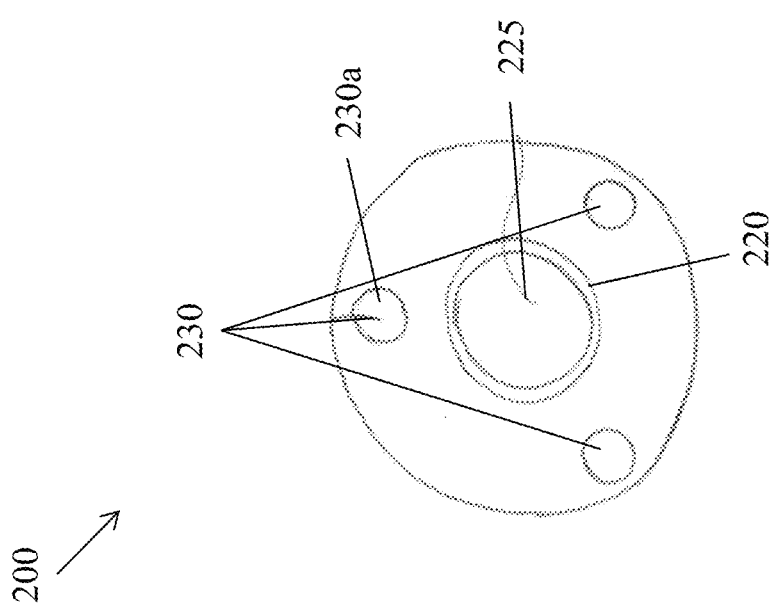
FIG. 2A illustrates a front view of an integrated CP and UT probe system in accordance with an alternate embodiment of the present application.

With reference now to FIGS. 2A-B, an integrated probe system 200 for conducting cathodic protection voltage readings and ultrasonic testing thickness measurements at an underwater surface in accordance with one or more implementations of the present application is provided. Integrated probe 200 comprises two main components which interlock together in such a way as to provide freedom of movement to the integrated probe to, upon contact, passively orient itself transverse to the inspection surface. An extruded outer gimbal 205 (or "static base") comprises the first component and its rear surface can be coupled to an ROV measurement arm. The extruded outer gimbal 205 includes a c-channel groove 206 centrally formed at the front surface of the outer gimbal, the groove having a mouth 208 and a pair of lips 209a, 209b that are sized and shaped for coupling the second component of integrated probe 200.

The second component includes a series of elements which are coupled together or integrally formed such that the combination acts as a single component that can couple to the outer gimbal 205. The second component can also be known as a probe carrier. A probe carrier describes the structure that houses the ultrasonic probe and provides electrically conductive material (e.g., electrically conductive voltage electrodes in the form of legs, a rim, or a surface) that encompass the CP and UT measuring tools that are oriented toward an inspection surface. In one or more embodiments, a probe carrier includes the elements of the integrated probe systems provided herein that have at least one degree of freedom of movement, and typically have two degrees of freedom (i.e., pitch and yaw). FIG. 2B illustrates one particular arrangement of elements which comprise the second component and its interlocking nature to the outer gimbal 205. In one or more embodiments, a ball caster 217 is provided that is sized and shaped to couple with the c-channel groove 206. The ball caster 217 shown in FIG. 2B, by way of example, is substantially spherical, though oval, ellipsoid, rectangular, square or other shapes can be contemplated. In one or more embodiments, the ball caster 217 is integrally formed with a first end of an articulated carrier 219. For example, the articulated carrier 219 and ball caster 217 can be a single metallic component made of stainless steel. In other embodiments, the ball caster 217 and articulated carrier 219 are separable components that can be coupled or decoupled for easy replacement. In one or more embodiments, a second end of articulated carrier 219 is integrally formed with the rear surface of inner gimbal 210 as a single molded piece. In other embodiments, the articulated carrier 219 and inner gimbal 210 are separate components that can be coupled or decoupled for easy replacement. In one or more embodiments, the articulated carrier 219 is conical, in which the broader end that connects to the inner gimbal 210 tapers toward the end that connects to the ball caster 217.

Advantageously, the groove 206 and the ball caster 217 flexibly couple such that the ball caster has some freedom of movement. In other words, after the ball caster 217 passes into mouth 208 to couple with outer gimbal 205, the ball caster 217 is not rigidly fixed in place, but rather can pivot within groove 206 subject to frictional forces at the inner walls of the groove. Further, the conical nature of the articulated carrier 219 allows the inner gimbal 210 to pivot accordingly with ball caster 217 in order to orient the front surface of the inner gimbal to the inspection surface. Thus, as the inner gimbal 210 contacts an inspection surface, the force imparted by the surface causes the inner gimbal to self-adjust until one or more electrically conductive legs 230 contact the inspection surface. The one or more electrically conductive legs 230 extend longitudinally away from the front surface of inner gimbal 210 and act as a voltage electrode to provide CP probe functionality. A corresponding reference electrode is electrically insulated and incorporated in integrated probe system 200, such as within outer gimbal 205, located at an outer surface of or within a ROV or its robotic arm, or in a subsea housing portion of the legs 230, in various embodiments. In some embodiments, the legs 230 are integrally formed with inner gimbal 210. For example, the inner gimbal 210 and legs 230 can be a single molded piece made of the same or similar material, such as stainless steel. In other embodiments, the legs 230 couple into ingresses defined by the molding of inner gimbal 210 and/or articulated carrier 219 (e.g., ingresses 115). In this way, the legs 230 can be replaceable and can be coupled or decoupled from integrated probe 200 for easy replacement. In one or more embodiments, the legs 230 are similar or the same as legs 130, and can be entirely electrically conductive, or can be limited to electrically conductive tips with a non-conductive coupling portion to the inner gimbal 210 (e.g., sub-sea housing 131 and tips 132). This arrangement of elements in the second component provides CP probe function for measuring surface voltage to integrated probe 200.

Integrated probe 200 further includes a sensor housing 220 and ultrasonic probe 225, which can be the same or similar to sensor housing 120 and ultrasonic probe 125. These elements function in concert to provide UT thickness measurement capabilities to integrated probe 200. In one or more embodiments, the sensor housing 220 is centrally located at the front surface of the inner gimbal 210. The legs 230 are then arranged about the sensor housing in an array such that when one or more of the legs contact the inspection surface, the ultrasonic probe 225 can perform UT thickness measurements. UT thickness measurements require that the ultrasonic probe 225 be in proximity with the inspection surface, so each of the legs 230 can only extend a short distance, if at all, beyond the sensor housing 220. For example, the ends of the legs 230 can extend 5-10 mm beyond the inner gimbal 210 than sensor housing 220 does.

In one exemplary embodiment, three electrically conductive legs are equally spaced in an array around ultrasonic probe 225. For example, each leg can be 120 degrees apart. In this embodiment, the ball caster 217 and the articulated carrier 219 provide two degrees of freedom to the inner gimbal 210 about two perpendicular axes, namely a vertical axis defined by the plane passing through the diameters of leg 230a and sensor housing 220, and a horizontal axis defined by the plane perpendicular to the vertical axis and also passing through a diameter of sensor housing 220. These axes can be similar or the same as the pitch plane or yaw plane identified above.

As described elsewhere herein, an underwater ultrasonic probe can be contained in sensor housing having a flexible membrane installed between a piezo-ceramic (or "transducer") crystal and the outer surface of the ultrasonic sensor housing. In one or more embodiments, electrically conductive media can be integrated into the rim or other parts of the sensor housing to provide CP probe function. The remainder of the sensor housing can be made of non-conductive material. In this way, an ultrasonic testing thickness measurement probe can function as an integrated CP/UT probe. In one or more embodiments, such integrated CP/UT probes can be installed in broader integrated probe systems. For example, an integrated CP/UT probe of this type can be installed in integrated probe system 100 or integrated probe system 200.

With reference now to FIGS. 3A-B, an integrated probe 300 for conducting simultaneous cathodic protection voltage readings and ultrasonic testing thickness measurements at an underwater surface is provided. Integrated probe 300 includes a sensor body 305 with an ultrasonic testing cable 310 coupled at a first end of the sensor body. The ultrasonic testing cable 310 provides data transfer of ultrasonic thickness measurements to a data processing system, which can be within a ROV or surface-side. An active ultrasonic element 315 is disposed at a second end of the sensor body 305, the second end being the end oriented toward the inspection surface. In one or more embodiments, ultrasonic element 315 is one or more piezo-ceramic crystals that emits and receives ultrasonic waves at a particular frequency. For example, the ultrasonic element 315 can operate at frequencies of 2.0 MHz, 2.25 MHz, 3.5 MHz, 5.0 MHz, or 7.5 MHz.

A flexible membrane 320 is adjacent to and spaced from the active element 315, thereby defining a gap 325 there between that is filled with couplant. The couplant can be a viscous liquid (e.g., water), gel, or a paste. In one embodiment, the flexible membrane 320 is made of latex rubber. The membrane 320 can be connected to sensor body 305 and a housing 330 of integrated probe 300 in various ways. For example, in response to manual urging, the membrane 320 can flex into a biased state with a reduced profile (e.g., a compression) in order to pass into a mouth defined by the housing 330, and upon release of the applied force at the membrane, the membrane restores to an unbiased state in which lips formed at the edges of the membrane engage with the interior of the housing and also engage with the exterior surface of sensor body 305. In one or more embodiments, the lips of the membrane 320 are sized and shaped to interlock with seats or grooves formed on the interior of the housing 330 of integrated probe 300. Depending on the resistance of the flexible membrane 320 to compression, in the unstable compressed state, the free ends will urge a greater or lesser amount toward the unbiased state. When attached to the interior of housing 330, this urging creates friction between the inner walls of the housing and the sensor body 305, which prevents the flexible membrane 320 from sliding longitudinally along the housing interior once coupled. This friction remains because the flexible membrane 320 is unable to fully return to its unbiased state while positioned within the groove or seat between the housing 330 and the sensor body 305, while the elastic restoring force continually applies pressure on the side walls of the groove. The housing 330 circumferentially surrounds at least a portion of sensor body 305. In one or more embodiments, the housing 330 is screwed onto the sensor body 305 via grooves on the inner surface of the housing 330 that receive corresponding threads molded onto the outer surface of the sensor body 305. In one or more embodiments, the housing is cylindrical and ring shaped to define an aperture therethrough in which the flexible membrane 320 passes.

In one or more embodiments, the housing 330 provides cathodic protection voltage probe functionality by acting as a voltage electrode. A corresponding reference electrode can be attached to an outer surface of or within a ROV or its robotic arm (not shown), in an electrically insulated manner, in various embodiments. In other embodiments, the reference electrode can be mounted within or to integrated probe 300. For example, the reference electrode can be housed within the sensor body 305, so long as it is electrically insulated from the voltage electrode (e.g., housing 330, rim 340, described below). Upon contact with an inspection surface, the housing 330 conducts the CP voltage of the surface to be inspected to a voltage measurement device (e.g., at the ROV or surface-side) via CP cable 335. CP cable 335 includes one or more conductive leads connected to and extending from an electrically conductive portion at the front surface (i.e., the surface oriented toward the inspection surface). This can be accomplished in two ways. In one or more embodiments, the entirety of the housing 330 can be made of conductive material, such as, for example, a knurled ring made of stainless steel or other alloys. This ensures that a voltage measurement can be made wherever the integrated probe 300 touches the inspection surface. In one or more alternate embodiments, the outer surface (or "rim") of the housing 330 can be limited to conductive material. In one or more embodiments, the rim is located adjacent to the flexible membrane 320 such that when the membrane contacts the inspection surface, the rim contacts simultaneously. For example, FIG. 3B illustrates a rim 340 that includes conductive material along the entirety of the surface surrounding the flexible membrane 320. It should be understood from the preceding discussion that the flexible membrane 320 is flush with the rim 340 or, if the membrane extends a distance beyond the rim, it can compress to enable the rim to make direct contact with an inspection surface in order to perform a CP measurement at the same time as a UT measurement. Embodiments of the integrated probe 300 do not include flexible membrane 320 designs that prevent the CP probe portion (e.g., housing 330, rim 340) from contacting the inspection surface.

Figure 4:
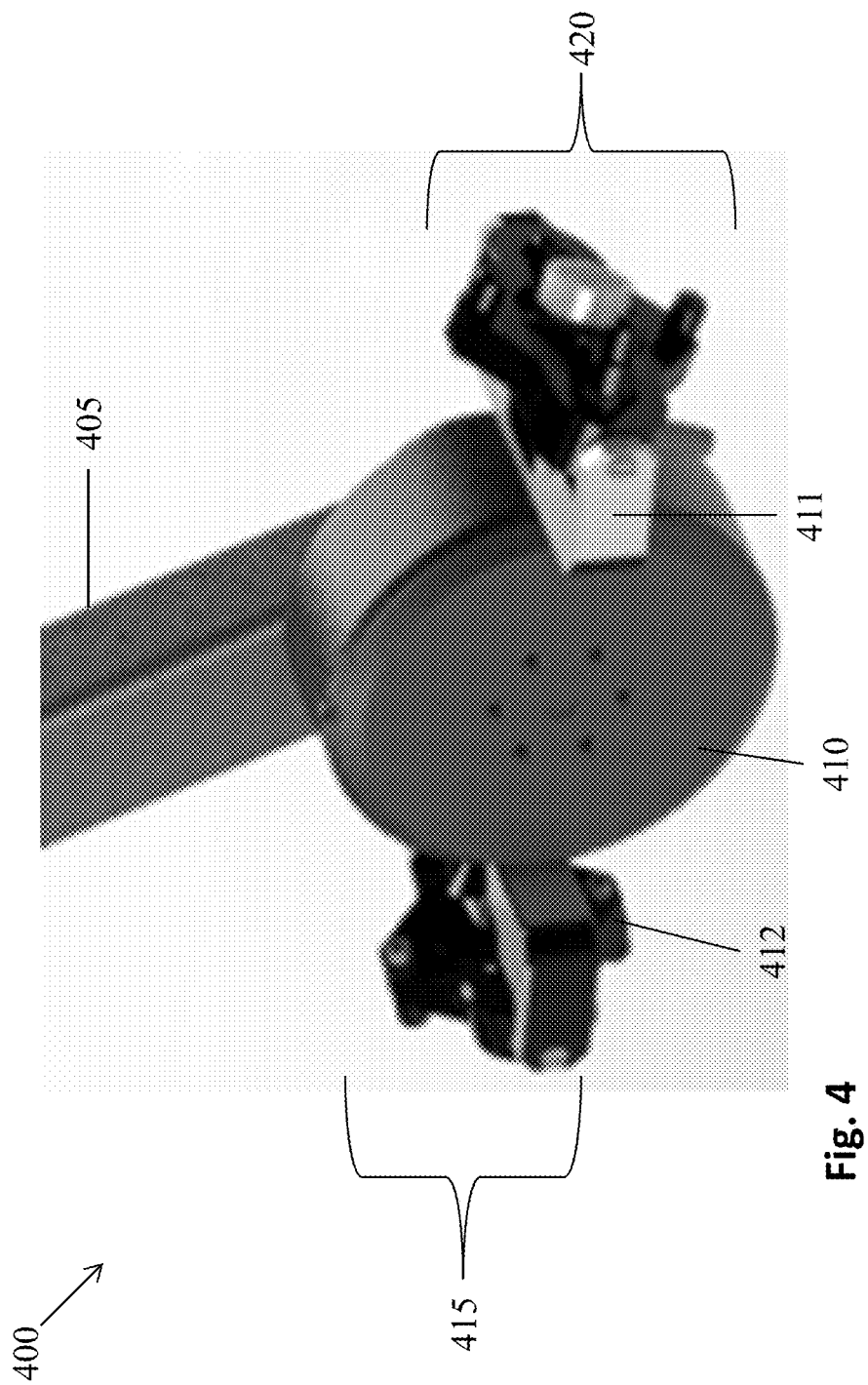
FIG. 4 illustrates a perspective view of an integrated CP and UT probe system in connection with a robotic arm in accordance with another alternate embodiment of the present application.

With reference now to FIG. 4, an integrated probe system 400 according to one or more embodiments is provided. A remotely operated vehicle (ROV) (not shown) includes at least one robotic measuring arm 405 having a rotatable end effector 410 at the free end of the robotic arm. The end effector 410 includes one or more probe attachment points for coupling various probe attachments. The attachment points can include modular frames that the probe attachment screws or snaps into, or include points for direct fixation to the end effector via a screw and threaded sleeve. Other similar attachment mechanisms can be used, as is known in the art.

The exemplary embodiment in FIG. 4 includes two diametrically opposed attachment points comprising modular frames 411, 412 sized and shaped to receive an integrated probe system, e.g., integrated system 100, integrated system 200. In other embodiments, the attachment points are separated by a certain angle, for example, 15, 30, 45, 60, 75 or 90 degrees. In one or more embodiments, a cathodic protection (CP) voltage measurement probe 415 and an ultrasonic thickness (UT) measurement probe 420 are coupled to the modular frames 411, 412 at the attachment points. In one embodiment, a combined CP and UT probe or probe system (e.g., integrated probe system 100, integrated probe system 200, integrated probe 300) is coupled to a single attachment point.

A motor (not shown) is housed within or mounted to the robotic arm 405 or end effector 410 in order to rotate the attachment points into desired positions. For example, the motor can be housed within the tip of the robotic arm 405 and be in mechanical connection with the end effector 410, as is known in the art. By actuating the motor and thereby rotating the end effector 410, the sensor facing the inspection surface can be swapped. For example, a ROV can bring the integrated probe system 400 into proximity with an inspection surface such that the CP probe 415 is oriented transversely to the surface to make a voltage reading. Thereafter, the motor rotates the CP probe 415 out from the inspection point and rotates the UT probe 420 in that same location to make a UT thickness measurement. After the UT thickness measurement is made, the motor can rotate the CP probe 415 and UT probe 420 back into their original pre-measurement positions. This cuts down on the delay between making CP and UT measurements.

In one or more embodiments, the rotation of either CP probe 415 or UT probe 420 occurs automatically as a result of software implementation identifying that a measurement has been made or is about to be made. For example, as soon as a CP voltage reading is complete, a computing device having a processor, which can be located with the housing of the ROV or located above-surface and communicatively coupled to the ROV, implements program code stored in a memory to instruct the motor to automatically shift the UT probe 420 into the location where the CP probe 415 had just made a measurement, without human intervention. In this way, the delay between taking a CP voltage reading and a UT thickness measurement can be reduced during underwater surface inspection.

While the exemplary embodiment disclosed in FIG. 4 contemplates a CP probe 415 and UT probe 420, other inspection sensors can be added in addition to the CP and UT probes or interchangeably fitted around the circumference of the actuated end effector 410 at the one or more attachment points in a modular fashion. For example, other sensors can include non-destructive testing sensors like eddy current or ACFM sensors, and visual sensors such as cameras or flashlights. The installation of visual sensors such as a camera with a flashlight on the body of the integrated probe aids in arm actuation control, thereby providing a more accurate alignment to the desired inspection surface.

Figure 5:
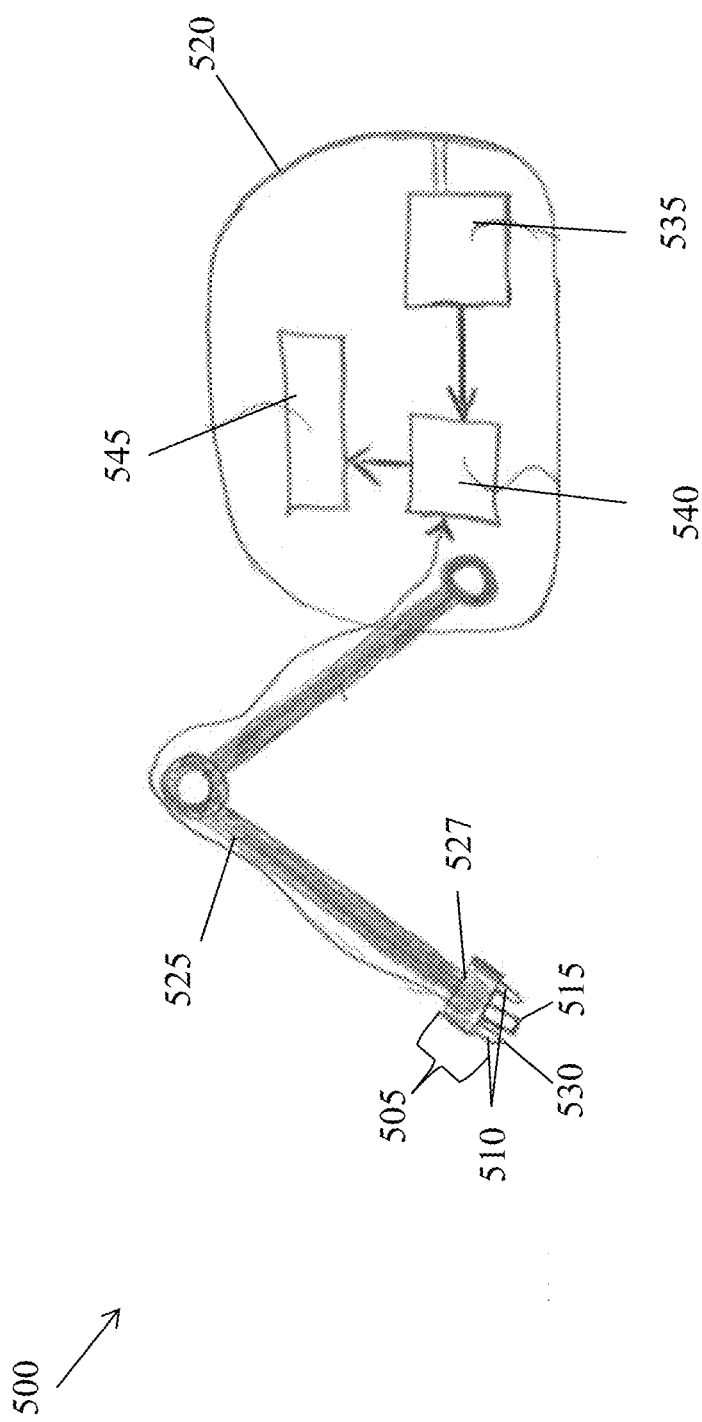
FIG. 5 is a simplified schematic diagram illustrating a side view of an inspection system implementing an integrated CP and UT probe system attached to an ROV in which the CP reference electrode and the CP voltage probe are split between the probe and the ROV body in accordance with at least one embodiment of the present application.

With reference now to FIG. 5, a system 500 for performing cathodic protection voltage readings and ultrasonic testing thickness measurements at an underwater surface is provided. In the example system 500, an integrated CP and UT probe system 505 is provided as described elsewhere herein (e.g., integrated probe system 100, integrated probe system 200, etc.), having a CP probe 510 and an UT probe 515. The integrated probe system 505 is coupled to a robotic arm 525 of a ROV 520 at an arm end-effector 527 located at the free end of the robotic arm. The ROV 520 can be any conventional ROV as is known in the art, including lighter, non-Work-Class ROVs. In one or more embodiments, the CP probe 510 includes a voltage electrode 530 at the arm end-effector 527 and a reference electrode 535 disposed at the outer surface of or within the ROV 520. In other embodiments, the voltage electrode 530 is disposed directly at the CP probe 510. For example, the voltage electrode 530 can be an electrically conductive tip (e.g., stainless steel) at an extended leg (e.g., legs 130) or an electrically conductive portion (e.g., rim 340) and the reference electrode 535 can be a silver/silver chloride half cell or other reference electrode exposed to water. Splitting the components of the CP probe 510 in this manner reduces the weight carried by the arm end-effector 527 and provides greater arm mobility without sacrificing electrical performance.

During the inspection process, when the system 500 contacts the underwater surface with the CP probe 510, a CP voltage measurement is made as provided elsewhere herein. A signal is then sent from the CP probe 510 along a cable within the robotic arm 525 to the ROV 520 where the signal is processed by a signal conditioner 540 to convert the raw electrical signals into a coherent form for output, such as in the form of a DC signal, as is known in the art. At the same time, the reference electrode 535, which is exposed to seawater and having a known electrode potential, makes a reference voltage measurement to the water and transfers a corresponding signal to the signal conditioner 540 to be processed in the same manner as the CP voltage signal. The signal conditioner 540 then calculates the differential voltage between the CP probe 510 and the reference electrode 535. The differential voltage output from the signal conditioner 540 is then transmitted as input to a data acquisition unit 545 where the voltage at the inspection surface can be recorded, reviewed, and analyzed. For example, the differential voltage is converted to a suitable digital or analog signal that can be processed and visualized to a user.

The mechanical aspects of ROV robotic arms (e.g., robotic arm 405, robotic arm 525) can also be improved in various ways. In one or more embodiments, floatation aiding material can be added near an arm-end effector to make the arm neutrally buoyant and to negate weight effects on the arm motors. In one or more embodiments, floatation aiding material can be integrated with an integrated probe or probe system as described elsewhere herein. Floatation aiding material can take the form of syntactic foam or floats made from, for example, polyurethane elastomers or resin and hollow glass microspheres. Other floatation aids can include umbilical buoyancy cords or the like.

Marine life growth at the inspection surface is a challenge to the efficacy of the system to take CP and UT measurements. It is therefore preferable to remove marine growth from the inspection surface before taking any measurements. In one or more embodiments, the integrated probe systems described herein can include cleaning systems mounted at the probe system. The cleaning systems can be placed at the arm-end effector of an ROV, such as at an attachment point. The addition of a cleaning system allows for simultaneous spot cleaning (of marine life on the underwater surface) and improved UT reading acquisition and measurement reliability upon contact. The cleaning systems can include conventional ROV cleaning tools such as water jet nozzles, cavitation jet nozzles, sand blasters or rotating brushes.

In one or more embodiments, the integrated probe systems described herein can include force or proximity sensors. A force sensor or a proximity sensor (e.g., infrared or acoustic) built in the integrated sensor body (e.g., at an attachment point, at an outer gimbal or an inner gimbal, or other position near to the CP and UT probes) can be used to aid in positioning the end effector on the targeted inspected surface to avoid harming the probe and/or the surface.

Notably, the figures and examples above are not meant to limit the scope of the present application to a single implementation, as other implementations are possible by way of interchange of some or all of the described or illustrated elements. Moreover, where certain elements of the present application can be partially or fully implemented using known components, only those portions of such known components that are necessary for an understanding of the present application are described, and detailed descriptions of other portions of such known components are omitted so as not to obscure the application. In the present specification, an implementation showing a singular component should not necessarily be limited to other implementations including a plurality of the same component, and vice-versa, unless explicitly stated otherwise herein. Moreover, applicants do not intend for any term in the specification or claims to be ascribed an uncommon or special meaning unless explicitly set forth as such. Further, the present application encompasses present and future known equivalents to the known components referred to herein by way of illustration.

The foregoing description of the specific implementations will so fully reveal the general nature of the application that others can, by applying knowledge within the skill of the relevant art(s) (including the contents of the documents cited and incorporated by reference herein), readily modify and/or adapt for various applications such specific implementations, without undue experimentation, without departing from the general concept of the present application. Such adaptations and modifications are therefore intended to be within the meaning and range of equivalents of the disclosed implementations, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

While various implementations of the present application have been described above, it should be understood that they have been presented by way of example, and not limitation. It would be apparent to one skilled in the relevant art(s) that various changes in form and detail could be made therein without departing from the spirit and scope of the application. Thus, the present application should not be limited by any of the above-described example implementations.

What is claimed:

1. An integrated probe suitable for performing cathodic protection voltage readings and ultrasonic testing thickness measurements substantially simultaneously at an underwater surface, comprising:
    an outer gimbal having a front surface and a rear surface;
    an inner gimbal coupled to the outer gimbal to provide at least one degree of freedom;
    an ultrasonic probe disposed within the inner gimbal; and
    one or more legs each having an electrically conductive tip and a subsea housing containing a reference electrode, each leg being coupled to and extending longitudinally away from the outer gimbal and arranged about the ultrasonic probe,
    wherein the one or more legs are passively adjustable in response to a force imparted when the one or more legs contact the underwater surface.

2. The integrated probe according to claim 1, wherein at least two legs each passing through ingresses defined by the inner gimbal.

3. The integrated probe according to claim 1, further comprising an articulated carrier having a first end integrally formed with the rear surface of the inner gimbal and a ball caster disposed at a second end, wherein the ball caster couples to the outer gimbal to provide the at least one degree of freedom to the inner gimbal.

4. The integrated probe according to claim 3, wherein the articulated carrier is conically shaped, wherein the first end tapers toward the second end.

5. The integrated probe of claim 3, the outer gimbal being a static base defining a c-channel groove sized and shaped to couple with the ball caster.

6. The integrated probe according to claim 1, wherein the electrically conductive tip is made of stainless steel.

7. The integrated probe according to claim 1, wherein the outer gimbal includes a c-channel groove centrally formed at the front surface of the outer gimbal.

8. The integrated probe according to claim 1, wherein the one or more legs are arranged about the ultrasonic probe as two pairs of diametrically opposed legs.

9. The integrated probe according to claim 1, wherein the at least one degree of freedom is provided by one or more rotational joints coupling the inner gimbal to the outer gimbal.

10. The integrated probe according to claim 1, wherein the at least one degree of freedom is provided by one or more rotational joints coupling the outer gimbal to an external carrier.

11. An integrated probe comprising:
    an outer gimbal having a front surface and a rear surface;

an inner gimbal coupled to the outer gimbal to provide at least one degree of freedom, the inner gimbal having a front surface defining a cavity therein;

a sensor housing seated in the cavity of the inner gimbal;

an ultrasonic probe disposed within the sensor housing, in which the ultrasonic probe includes a flexible membrane arranged about a transducer crystal such that a gap is defined therebetween and filled with a couplant; and a voltage electrode communicatively coupled to a reference electrode, wherein the voltage electrode is disposed at an electrically conductive portion of the integrated probe, and the reference electrode is electrically insulated from the voltage electrode.

12. The system according to claim 11, wherein the reference electrode is a silver/silver chloride half-cell.

13. The system according to claim 11, wherein the inner gimbal is shaped to define one or more ingresses that pass crosswise between the front and rear surfaces of the inner gimbal, and the electrically conductive portion comprises one or more legs each having an electrically conductive tip and extending longitudinally away from the outer gimbal via the one or more ingresses and arranged about the ultrasonic probe.

14. The system according to claim 13, wherein the voltage electrode is one or more of the electrically conductive tips of the one or more legs.

15. The system according to claim 13, wherein the reference electrode is disposed within one of the one or more legs.

16. The system according to claim 13, wherein the one or more electrically conductive legs are passively adjustable.

17. The system according to claim 13, wherein the reference electrode is disposed within the outer gimbal.

18. The system according to claim 11, wherein the electrically conductive portion is disposed at the inner gimbal.

19. The system according to claim 11, wherein the reference electrode is exposed to water.

20. The system according to claim 11, wherein the reference electrode is disposed within a remotely operated vehicle.

* * * * *